July 24, 1973 W. H. JESSEL, JR., ET AL Plant Pat. 3,373
CHRYSANTHEMUM PLANT
Filed May 17, 1971
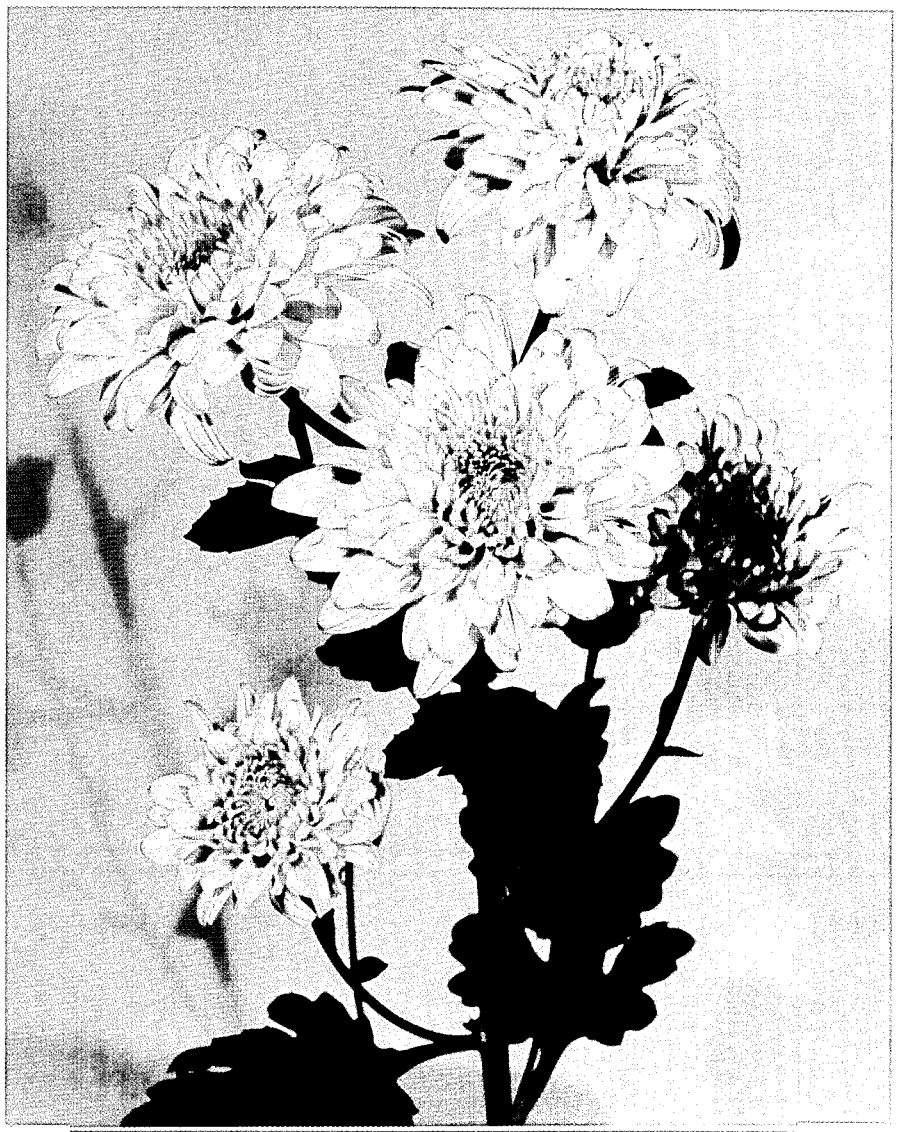
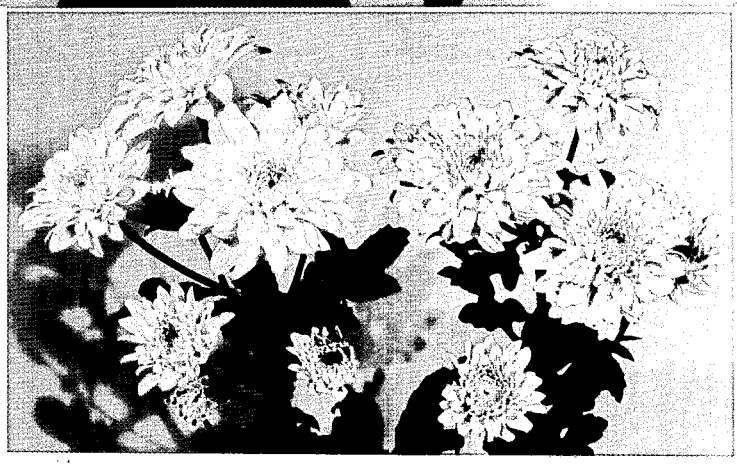

United States Patent Office

Plant Pat. 3,373
Patented July 24, 1973

3,373

CHRYSANTHEMUM PLANT

Walter H. Jessel, Jr., Doylestown, and William E. Duffett, Akron, Ohio, assignors to Yoder Brothers, Inc., Barberton, Ohio

Filed May 17, 1971, Ser. No. 144,190
Int. Cl. A01h *5/00*
U.S. Cl. Plt.—80 1 Claim

The present invention comprises a new and distinct cultivar of chrysanthemum plant which is a sport of the unpatented cultivar known commercially in the United States as Telstar.

The new cultivar is similar in many respects to Telstar, having the same characteristics as Telstar of:

1. Plant habit.
2. Flowering response.
3. Flower size and form.

The new cultivar is distinguished from Telstar by the following characteristics:

in Barberton, Ohio. The response time, blooming period, color, and total vigor may vary significantly with varying environmental conditions such as temperature, day length, and light intensity. Suggested flowering in the northern and western United States is from October through mid-June; coastal California, September through May; Florida, mid-October through May.

The accompanying drawing shows the unique characteristics of the new cultivar, the color being as nearly true as possible with color illustrations of this type. In the drawing, the new cultivar appears on the top, and in the comparison photograph at the bottom of the drawing, the new cultivar appears on the right and the cultivar Telstar on the left.

Color references are made to the Munsell Color Book, 1963 edition, and comparisons are made with the cultivar Telstar. Where only a single value or description appears for the new cultivar, the same applies also to the parent.

Botanical classification: *Chrysanthemum morrifolium*

| | Deep Telstar | Telstar |
|---|---|---|
| Bloom: | | |
| Size | 3¼" | |
| Fully expanded | 5" | |
| Borne | Clusters on elongated pedicels | |
| Stems | Strong | |
| Form | Decorative | |
| Permanence | 10–14 days | |
| Color: | | |
| Center of flower | Lavender 2.5RP6/6 | Pale lavender 5RP9/2. |
| Base of petals | Lavender 2.5RP6/6 to light lavender 2.5RP7/4 | Pale lavender 2.5RP9/2 to pale lavender 5RP9/2. |
| Inside of petals | do | Do. |
| Reverse of petals | Pale lavender 2.5RP8/4 | Very pale lavender 5RP9/1. |
| Tonality from a distance | Lavender | Light lavender. |
| Discoloration | Light lavender 2.5RP7/4 | Pale lavender 5RP9/2. |
| Petals: | | |
| Texture | Smooth | |
| Appearance and form | Open at base, board shallow ridged keel, tapering to a blunt point. | |
| Arrangement | Composite, whorled on a single receptacle | |
| Persistence | Resist shatter | |
| Fragrance | Typical chrysanthemum | |
| Reproductive organs: | | |
| Stamen | None | |
| Anthers | do | |
| Pollen | do | |
| Arrangement | Clustered in center of flower, if present | |
| Styles | Present ray florets | |
| Length | Short | |
| Ovaries | At the base of petal attached to receptacle | |
| Plant: | | |
| Form | Herbaceous | |
| Growth | Upright | |
| Height | Approximatley 43"–47" when grown as a single stem crop, given 3 to 5 long day weeks and 13 to 15 weeks total crop time for the various seasons of the year as defined in the timetables published by Yoder Bros., Inc. | |
| Spread | None when grown single stem to moderate when pinched | |
| Foliage: | | |
| Top side | Very dark green, 10GY2/4 | |
| Size | 7½" long, 5" wide | |
| Quantity | Numerous | |
| Shape | Spatulate lobed | |
| Texture | Smooth | |
| Ribs and veins | Very prominent | |
| Edge | Deeply indented | |
| Serration | Coarse | |
| Underside | Light green 7.5GY5/4 | |
| Stipules | Very prominent | |

1. More intense lavender flower color.
2. Flower color more attractive when parent fades.
3. Longer period of value—October to mid-June vs. mid-October through April of parent.

The new cultivar was selected from a flowering block of the parent cultivar at Barberton, Ohio; and when asexually reproduced by cuttings at Barberton, Ohio, has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse

We claim:

1. A new and distinct cultivar of chrysanthemum characterized particularly as to its uniqueness when compared to the parent cultivar Telstar by its more intense lavender flower color; a superior flower color retention, with the lavender color being darker and more attractive than parent when fading occurs; and by its longer period of value, October to mid-June, as compared with mid-October through April of the parent cultivar.

No references cited.

ROBERT E. BAGWILL, Primary Examiner